United States Patent [19]
Kross

[11] 3,980,084
[45] *Sept. 14, 1976

[54] OSTOMY GASKET

[75] Inventor: Robert D. Kross, Bellmore, N.Y.

[73] Assignee: Hydro Optics, Inc., New York, N.Y.

[ * ] Notice: The portion of the term of this patent subsequent to Apr. 15, 1992, has been disclaimed.

[22] Filed: Mar. 3, 1975

[21] Appl. No.: 554,709

Related U.S. Application Data

[63] Continuation-in-part of Ser. No. 432,068, Jan. 9, 1974, Pat. No. 3,877,431, and a continuation-in-part of Ser. No. 495,822, Aug. 8, 1974.

[52] U.S. Cl. .................. 128/283; 128/DIG. 24; 260/16
[51] Int. Cl.² ........................................... A61F 5/44
[58] Field of Search ................. 128/283, DIG. 24; 260/89.5 R, 86.1 R, 29.6 WB

[56] References Cited
UNITED STATES PATENTS

| | | | |
|---|---|---|---|
| 2,976,576 | 3/1961 | Wichterle et al. | 260/89.5 R |
| 3,218,305 | 11/1965 | Kieble | 260/86.1 R |
| 3,220,960 | 11/1965 | Wichterle | 260/86.1 R |
| 3,351,061 | 11/1967 | Nolan | 128/283 |
| 3,361,858 | 1/1968 | Wichterle | 264/1 |
| 3,515,579 | 6/1970 | Shepherd et al. | 260/86.1 R |
| 3,640,741 | 2/1972 | Etes | 128/283 |
| 3,647,736 | 3/1972 | Ewell | 260/29.6 WB |
| 3,700,761 | 10/1972 | O'Driscoll et al. | 260/29.6 WB |
| 3,712,304 | 1/1973 | Marsan | 128/283 |
| 3,721,657 | 3/1973 | Siderman | 260/29.6 WB |

*Primary Examiner*—Aldrich F. Medbery
*Attorney, Agent, or Firm*—Kenyon & Kenyon Reilly Carr & Chapin

[57] ABSTRACT

An improved ostomy sealing gasket for application to the opening between the intestinal or urethral stoma of the patient and a post-surgical external pouch. The sealing gasket is made from a hydroxyalkyl acrylate or methacrylate with an alkylene glycol or polyalkylene glycol in the presence of a reducing agent and water. Embodiments designed for higher absorptive capacity also include an absorptive material such as natural or synthetic gums or a cellulosic material.

7 Claims, No Drawings

OSTOMY GASKET

This application is a continuation-in-part of U.S. application Ser. No. 432,068, filed Jan. 9, 1974, (now U.S. Pat. No. 3,877,431), and U.S. application Ser. No. 495,822, filed Aug. 8, 1974.

This invention relates to post surgical ostomy devices and more particularly to sealing devices utilized between the stoma of the patient and the external pouch to prevent the escape of waste materials.

A surgical procedure such as a colostomy, ileostomy or urethrostomy comprises the formation of an opening, or stoma, in the wall of the intestine, urethra, etc., which opening extends through the patient's skin. The stoma provides a means of communication between the inside of the intestine, urethra, etc., and the external world through which various bodily excretions such as fecal material and urine may intermittently pass. Therefore, it is necessary for the post surgical patient to wear a collecting receptacle for this material, such as a pouch or bag, attached to the stoma, for the remainder of his life.

It is imperative that there be a sufficient seal between the patient's skin and the collection receptacle. Due to the noxious and obnoxious nature of the waste materials which pass through the stoma, it is extremely desirable that none of the materials be allowed to leak past the seal. These materials are not only personally unpleasant, but are irritating to the skin and can cause marked irritation and excoriation if allowed to come into repeated or continuous contact with the skin. It is customary to utilize a flexible gasket as such a seal. This gasket is designed to fit snugly around the stoma, without constricting the opening. The fit should be sufficiently snug, and the gasket material sufficiently flexible to provide a leak-proof seal around the stoma, which is often irregular and uneven.

The gasket should preferably have certain special properties in order to function in a satisfactory manner. It should be sufficiently soft and flexible to be able to change shape in conformity with bodily movement and peristaltic action without leakage of material. It should not swell upon contact with moisture to the extent that such swelling causes the gasket to lose its shape and therefore its sealing ability. It should not shrink under use conditions, as shrinking could cause constriction and possibly even strangulation of the stoma. It should be stretchable, with a moderate amount of recovery, so that a centrally located hole in the gasket will be able to grip the stoma firmly and thereby conform to its irregular surface and provide full leak protection. It should be stable in the presence of acids, bases, enzymes and other materials which may be found in intestinal and urinary discharges. It should be non-allergenic, non-irritating, and non-sensitizing. It should be sufficiently tacky to firmly adhere to both the patient's skin and the collection receptacle without the use of additional adhesives. It should be able to retain a relatively fixed quantity of water, irrespective of the amount of moisture with which it is in contact. It should permit healing of the skin under the gasket. Additionally, it is desirable if it possesses visual appeal, such as optical clarity, freedom from odor, and the possibility of re-use, after rinsing.

It has been generally the practice to manufacture these gaskets from natural gums, primarily karaya gum, which may be admixed with other gums such as guar gum and locust bean gum. While such gums can be useful for absorbing moisture, gaskets made primarily from this type of material have a number of undesirable features. First, gaskets made primarily from this type of material are generally brown and opaque. Secondly, they tend to continuously absorb water during use, eventually becoming gelatinous and useless after several days' use. Moreover, prior to use, gaskets made from this type of material tend to be relatively stiff and are therefore difficult to shape properly to conform with the stomal opening. In addition, after exposure to water their surface develops a rather slimy feel. This diminishes any natural tackiness which they may possess and may necessitate the use of an adhesive to cause them to adhere to the skin and the collection receptacle.

Other typical materials which have been used to form ostomy gaskets include such water absorbing materials as pectin, gelatin, sodium carboxymethylcellulose and mixtures thereof. As these materials continually absorb water, they rapidly become gelatinous and useless as gasket materials.

It is thus an object of this invention to provide an improved ostomy gasket which will have a relatively long life and which will be superior to previous ostomy seals in respect of the above-mentioned criteria. It is a further object to provide a more effective seal against leakage of intestinal and urinary wastes. It is also an object to provide an ostomy gasket which is sufficiently tacky to require no additional adhesives.

It is a still further object to provide a novel hydrophilic polymeric material which is chemically resistant while being generally non-irritating to the human body. This hydrophilic material is thus useful for a variety of applications whereby an appliance must remain in contact with the skin or mucous membrane.

Further objects will become apparent from the following disclosure.

Ostomy sealing gaskets according to this invention may be of any convenient size and shape. Generally such gaskets are in the form of smooth flat sheets of material ranging in thickness up to about one-fourth inch, with thinner material being preferable.

The material is generally in the form of a circular disk of two to three inch diameter. This size can be varied depending on the type and size of the stomal opening, the condition of the skin surrounding the stoma, etc. It may also be in the form of a square, oval or other shape.

A hole extending through the sheet of material is made to receive the stoma of the patient. This is of a size which will fit snugly about the intestinal or urethral stoma. This hole is generally centered in the disk of material. In the case of intestinal stomata, these holes are generally about one-half inch in diameter.

While it is a feature of this invention that the ostomy gaskets made from the unique materials of the invention are sufficiently tacky to adhere to the skin, and to the collection receptacle, it is also possible to apply to either or both faces of the gasket, an additional adhesive. This adhesive may be any of the usual types designed for this purpose which are non-irritating to the skin.

Both faces of the gaskets of this invention are preferably covered with a standard release paper. The use of a release covering facilitates the ease of application of the gasket to the skin area and pouch. It also aids in maintaining the cleanliness and sterility of the gasket during such application.

While it is generally unnecessary, the gasket may be sterilized by standard methods prior to use. The hydrophilic polymers of this invention are able to withstand the temperatures necessary to sterilize the gaskets. Additionally, after use the gaskets of this invention may be washed, resterilized, air-equilibrated and then reused without any substantial loss of beneficial properties. Generally, whenever the gaskets of this invention are sterilized, it is preferable to air-equilibrate them before use. Otherwise, they may become whitish, and their tackiness may be diminished.

The polymers of this invention are formed by the polymerization of a hydroxyalkyl acrylate or methacrylate in the presence of a polyalkylene glycol, reducing agent, or chain terminator, and water. It is important to use a relatively pure grade of acrylic monomer. It is also preferable to utilize a reaction catalyst, or initiator. Where gaskets capable of absorbing higher quantities of moisture are required, the invention also comtemplates addition of natural or synthetic gums or cellulose type materials to increase absorptive capacity. Depending upon the type and amount of such materials employed, alkylene glycols or glycerine may be substituted for the polyalkylene glycol used in gaskets having less capacity.

The acrylic starting materials which are useful consist of hydroxyalkyl acrylates, hydroxyalkyl methacrylates, and mixtures thereof. It is necessary that the particular compound or mixtures utilized be at least partially water soluble. Thus, the length of the alkyl chain should generally be no more than about four carbon atoms in length. Examples of acrylic starting materials useful in the formulations of this invention are hydroxyethyl acrylate, hydroxypropyl acrylate, hydroxyethyl methacrylate, and hydroxypropyl methacrylate.

The acrylic starting materials polymerize to a matrix which is resistant to chemical attack. Such a polymer matrix will be resistant to acids, bases, enzymes, and other chemicals which are present in the intestinal tract. Additionally the polymeric acrylates can withstand the temperatures necessary to sterilize the gasket in an autoclave.

The monomeric acrylic material is polymerized with a polyalkylene glycol, such as polyethylene glycol, polypropylene glycol, and hexylene glycol. In the normal formulations, these materials should be of a moderate molecular weight. Generally liquid polyalkylene glycols are utilized where their average molecular weight should be in the range of about 120 to about 800, and preferably from about 200 to about 650. However, in the case of formulations designed for higher absorptive capacity which employ natural or synthetic gums or cellulosic materials and the like, the average molecular weight of the polyalkylene glycol used is typically reduced below these ranges, and in some cases glycerine or propylene glycol is used, depending upon the properties and amount of such gums or cellulosic materials used, as discussed below.

Where no gums or cellulosic materials are included in the formulation, the use of a polyalkylene glycol with too high an average molecular weight can render the resulting polymeric material deficient in equilibrium water content. A gasket manufactured from such material would be too stiff to provide a good seal around the stomal opening. The use of a polyalkylene glycol with too low an average molecular weight could result in the formation of a material which is too soft and which might lose the glycol through solubility in bodily fluids.

The glycolic material imparts a flexibility and softness to the polymer product. It increases the internal lubricity of the polymer matrix, thereby allowing the gaskets made therefrom to develop a proper conformity to the skin. The increased flexibility allows a close fit between the gasket and the stoma without the danger of breaking the seal during body movements.

The glycolic material also increases the water-holding capacity of the polymer matrix. The tendency of the polymeric materials to recover their original or pre-use shape is also reduced. If allowed to recover the pre-use shape, the gaskets would provide too tight a seal causing constriction of the stoma. The gasket should have some recovery, so that when it is stretched to fit over the stoma and then released, it will snugly grip the stoma. However, too great a recovery can cause a constriction of the stomal opening.

Apparently, the glycolic starting material alters the properties by interfering with the hydrogen bonding between carboxyl groups and hydroxyl groups on adjacent acrylate chains. Thus, the interchain attractions are reduces, and a greater quantity of water can adhere to these attractive sites.

An essential component of the reaction mixture is a water-soluble reducing agent or chain terminator. Examples of suitable reducing agents are hydroquinone, ascorbic acid, araboascorbic acid, erythorbic acid and mixtures thereof.

The inclusion of the reducing agent in the formulation serves to limit the chain size of the polymer, and thereby prevents too great a molecular weight polymer from forming. In this manner, the requisite degree of fluidity, softness and tackiness is obtained.

Generally utilizing a weaker reducing agent than those listed above, or an insufficient quantity of them, will allow the polymer chains to become too long. The resulting product will tend to be firm and hard with little or no tackiness. A reducing agent which is too strong may inhibit initiation of polymerization, which can lead to only polymer fragments being formed, which would have too low a molecular weight.

It is also essential that the polymerization reaction be carried out in the presence of water. In this manner, a considerable quantity of water is absorbed into the polymer matrix during the polymerization reaction. This absorbed water generally is attached by means of hydrogen bonding to reactive carboxyl and hydroxyl groups. The inclusion of the water aids in preventing the formation of strong interchain hydrogen bonds, the formation of which could cause a detrimental increase in rigidity in the resulting product.

The gasket polymers of this invention designed for normal absorptive capacity (not employing gums or cellulosic materials), are usually made by utilizing from about 75 parts to about 175 parts of acrylic material, from about 75 parts to about 150 parts of glycolic material, and from about 0.05 parts to about 1.0 parts of reducing agent, all per 100 parts of water. It is preferred that the acrylic material be utilized in the range of about 85 parts to about 115 parts, the glycolic material in the range of about 75 parts to about 100 parts, and the reducing agent in the range of about 0.1 parts to about 0.5 parts, although it is preferred that the amount of reducing agent be nearly equal to or greater than the amount of any reaction initiator or catalyst used.

The reactive amounts of each of the components may be adjusted within these ranges to provide polymeric materials with varying degrees of softness, tackiness, memory, water-holding capacity, etc.

If excess acrylic starting material is utilized, the resulting polymeric material will have a decreased flexibility and too great a recovery. A sufficient quantity of water will not be incorporated into the polymeric matrix to provide the desired internal lubricity and the resulting material will be rubbery.

The utilization of an insufficient quantity of acrylic starting material can lead to a polymeric material which is unduly soft and which has excess water and polyalkylene glycol entrapped in the matrix. During use, these materials will be exuded, which will reduce the tackiness and effectiveness of the gasket.

If the quantity of acrylic starting material is substantially less than the indicated range, any resulting polymer may be only a semi-solid mass, which would be completely useless as a gasket material.

If an excess of glycolic starting material is utilized, the resulting polymeric material will not be tacky and may have a slippery or slimy feel to it. The use of an insufficient quantity of glycolic material can lead to a rubbery product, which would possess too much of a tendency to recover its pre-use shape.

It may be advantageous to incorporate into the reactant solution a small quantity of a reaction initiator. This compound may be selected from among the known free-radical generators, such as benzoyl peroxide, 2,5-dimethyl-2,5-bis (2-ethyl hexanoyl peroxy) hexane or similar organic peroxide initiators, or potassium persulfate and similar initiators.

The use of a reaction initiator is not essential to the process of this invention. Generally, the chain terminator also will function as a mild initiator within the range of temperatures useful in producing the polymers of this invention. When omitting the reaction initiator, however, the reaction may proceed somewhat slower and it may be desirable to carry out the polymerization at somewhat higher temperatures to avoid excessive chain lengths if the reaction proceeds too slowly.

Up to about 1% of reaction initiator may be utilized. It is preferable that about 0.4% be utilized in the formulation. As the use of an excess amount of initiator will have an effect on the product similar to that produced by carrying out the reaction at too high a temperature, it is preferable to reduce the quantity of initiator utilized when using a higher temperature, and to increase the quantity at a lower reaction temperature.

The compositions of this invention are polymerized generally by the following process.

The reducing agent is mixed into the water until dissolved.

The acrylic component is then mixed into the solution, with stirring until dissolved.

Then, in similar manner, the glycolic component is added to the solution.

While the order of mixing the above reactants into the water is not critical, it is preferable for each component to be completely dissolved prior to the addition of the other materials.

The reaction initiator is then added and the solution is deposited into appropriate molds.

It is preferable that the reactants be cooled prior to use. If the reactants are at room temperature when mixed, it is possible that the polymerization reaction may begin prior to depositing the solution into the appropriate molds. Generally, it is sufficient to cool the reactants to the range of ordinary refrigerator temperature, or about 1°C. to about 5°C.

Temperatures and times for polymerization depend upon the types and amounts of catalyst or initiator and reducing agent used. If the polymerization reaction is carried out at too low a temperature for a given catalyst and reducing agent, the reaction will proceed relatively slowly. This will enhance the formation of long polymeric chains thereby producing a product which possesses insufficient tackiness. It will also be rubbery and have an undesirably high recovery.

Polymerization carried out at too high a temperature for a given catalyst and reducing agent will produce a product which is too soft and unduly sticky. It may also produce some bubbles in the product due to the vaporization of the water.

For materials polymerized with the preferred amounts of a reducing agent and an organic peroxide catalyst, such as 2,5-dimethyl-2,5-bis (2-ethyl hexanoyl peroxy) hexane, the molds are heated gently, i.e., in an oven at a temperature of about 75°C. to about 95°C., and preferably about 80°C. to about 90°C. for about 10 minutes to an hour. With the same amounts of a reducing agent and potassium persulfate as a catalyst, the molds can be cured at lower temperatures between about 20°C. and about 40°C., such as at room temperature for about 30 minutes to about 3 hours, although it is desirable to subject molds initially cured at room temperature to a final curing in an oven at temperatures of about 75°C. to about 95°C. for about 10 minutes to an hour.

It is possible to produce materials having varying degrees of tackiness by varying the polymerization temperature. Generally, the lower the temperature, the less tacky is the product. If the temperature is maintained for too long a time, some water will be lost from the material.

In certain applications of the ostomy gasket, especially where the user has excess leakage of liquid from his stomal opening, such as in the case of a urethrostomy or ileal conduit bladder by-pass, it is desirable to increase the capacity of the gasket to absorb water and thereby prevent the loss of tackiness which accompanies the over-saturation of the gasket.

To accomplish this, it has been found useful to incorporate into the prepolymer mixture used to fabricate the gasket material a natural or synthetic gum, polymer, or certain specilized products, which is capable of absorbing excess water and swelling thereby. Being entrapped in the gel matrix of the gasket, the absorbing materials cause a swelling of the gasket but not a concomitant degradation of the structural integrity of the product, such as would occur if the absorbing material formed the major component of the gasket body. The basket so-produced thereby retains its desirable properties of cohesiveness, sealability, elasticity, and tackiness.

Examples of absorptive materials which can serve in this capacity are karaya gum, gum acacia, guar gum, hydroxyethyl cellulose, methyl cellulose, microcrystalline cellulose, and fumed silica. At low levels of inclusion below about 10% by weight to the overall mixture the material can be included into the normal gasket formula without significant interference with formula compatibility and polymerization. At higher levels above about 10% by weight to the overall mixture it is necessary to modify the formula by reducing the average molecular weight of the glycol component. This modification, for example, may require the substitution of a shorter-chain glycol (e.g., glycerine or propylene glycol) for the polyethylene glycol, where the higher polarity of the smaller glycols is needed to better solvate the moisture-absorbing material in the prepolymer matrix. The use of shorter chain alkylene glycols in formulas having over about 10% by weight of gums or cellulosic materials also permits the use of relatively less water. In such formulations, from about 100 parts to about 500 parts of acrylic starting material, and from about 100 parts to 900 parts glycolic material, can be used per 100 parts water. It is preferred that acrylic material be utilized in the range of about 200 parts to about 400 parts, and glycolic material in the range of about 300 parts to about 700 parts, all to 100 parts water.

After the molds are cured, the resulting material is cooled and is ready for use. For the manufacture of the ostomy gaskets of this invention, it is preferably covered with a release paper, and a hole is cut or punched in the center.

The following illustrative examples will further illustrate this invention:

EXAMPLE 1

Dissolve 0.45 grams of d-araboascorbic acid in 100 ml of water. Add 100 ml of hydroxyethyl methacrylate to the above solution, with stirring, and then add 80 ml of polyethylene glycol having an average molecular weight of about 400. After thoroughly mixing, add 1.2 ml of 2,5-dimethyl-2,5-bis (2-ethyl hexanoyl peroxy) hexane.

Pour the resulting solution into cylindrical glass molds, two inches in diameter, to a depth of one-eighth inch. Place the molds into an oven and maintain them at a temperature of 88°C. for 45 minutes. Cool the polymeric material, remove from the molds, and cover with release paper. A ½-inch diameter hole is punched in the center of each disc to make the finished gasket. The resulting gasket possesses the aforementioned desirable properties.

EXAMPLE 2

The procedure of Example 1 is repeated using hydroxypropyl methacrylate and a polyethylene glycol of average molecular weight of about 600. This produces a gasket which is slightly whitish due to a small amount of excess water, but which is otherwise similar to the gasket produced in Example 1. The evaporation of water from this product leaves a crystal clear gasket, which is then covered with release paper.

EXAMPLE 3

The procedure of Example 1 is repeated except that the polymerization temperature is 65°C. The resulting gasket is too rubbery and lacks the tackiness necessary for proper use as a post-surgical gasket.

EXAMPLE 4

The procedure of Example 1 is repeated utilizing a temperature of 105°C. The gasket has small bubbles throughout and is very soft and tacky.

EXAMPLE 5

The procedure of Example 1 is repeated, except that only 40 ml of polyethylene glycol is utilized. The resulting product is rubbery and has very little tackiness.

EXAMPLE 6

The procedure of Example 1 is repeated, except that 60 ml of hydroxyethyl methacrylate is utilized. The resulting gasket is soft, with a generally slippery feel.

EXAMPLE 7

Dissolve 0.65 gm of l-ascorbic acid in 60 ml of water. Add 75 ml of hydroxyethyl methacrylate to the above solution, with stirring, and then add 59 ml of polyethylene glycol (average molecular weight of 400). While thoroughly mixing, add 10 gm of karaya gum powder slowly, and cool the mixture in an ice bath. Then add 0.937 gm of potassium persulfate and mix for about 45 seconds, and pour the resulting dispersion into cylindrical glass molds, two inches in diameter, to a depth of three-sixteenths inch. Let the molds gel at room temperature for 1 hour, and then place them in a 90°C. oven for 25 minutes for final cure. Cool the mold, remove the discs, and cover with release paper. The resulting gasket material has the desirable properties of tack, elasticity, sealability, and flexibility with augmented moisture absorption properties.

EXAMPLE 8

Mix 5 ml of glycerine, 3 ml of hydroxyethyl methacrylate, and 1 ml of water in a beaker. Add 0.5 gms ascorbic acid and slowly stir in 3 gms of karaya gum powder. Add 3 drops of 2,5-dimethyl-2,5-bis (2-ethyl hexanoyl peroxy) hexane. Pour the mixture into cylindrical glass molds, 2 inches in diameter, to a depth of one-fourth inch. Place in an oven at 88°C. for 30 minutes to cure. Cool, remove from the molds, cut a ½-inch diameter hole in the center of each disc, and cover the finished gasket with release paper. The product has the properties of tackiness, flexibility, sealability, mild stretchability and recovery, and a greatly enhanced capacity for moisture uptake. A gasket of this type can absorb water to more than three times its original weight without losing structural integrity.

EXAMPLE 9

Dissolve 1.5 gms of methyl cellulose in 28 ml of water at 90°C. Cool while stirring, and gradually add 23.6 ml of polyethylene glycol (molecular weight 400). Then add a mixture of 0.261 gm of erythorbic acid in 30 ml of hydroxyethyl methacrylate. Finally stir in 0.15 gm of potassium persulfate dissolved in 6 ml of water and pour into 2-inch cylindrical plates to a height of one-eighth inch. Let cure at room temperature (25°C.) for two hours under a nitrogen atmosphere, and then place in a 90°C. oven for 15 minutes. The resulting gasket, when stripped from the mold, is transparent and has the desired properties of tack, flexibility, elasticity, and increased moisture uptake as compared with a formulation prepared without the methyl cellulose.

What is claimed is:

1. An ostomy sealing gasket designed to provide a seal between a post-surgical drainage pouch and the skin around the stomal opening comprising a flat sheet of polymeric material including an opening therethrough to receive the stoma of the patient, wherein said polymeric material comprises the reaction product of:

a. a compound selected from the group consisting of a hydroxyalkyl acrylate, a hydroxyalkyl methacrylate and mixtures thereof;

b. a glycolic compound selected from the group consisting of a polyalkylene glycol, an alkylene glycol, glycerine, and mixtures thereof;

c. a water-soluble reducing agent; and d. an absorptive material for absorbing excess water; the reaction carried out in the presence of water.

2. An ostomy sealing gasket according to claim 1, wherein the glycolic compound is a polyalkylene glycol having an average molecular weight of about 200 to about 650, and the amount of absorptive material is less than 10% by weight of the total reaction mixture.

3. An ostomy sealing gasket according to claim 2, wherein the acrylate component is utilized in the range of about 75 parts to about 175 parts, the glycolic component in the range of about 75 parts to about 150 parts, and the reducing agent in the range of about 0.05 part to about 1.0 part, all parts per 100 parts water.

4. An ostomy sealing gasket according to claim 1, wherein the glycolic material is glycerine, and the amount of absorptive material exceeds 10% by weight of the total reaction mixture.

5. An ostomy sealing gasket according to claim 4, wherein the acrylate component is utilized in the range of about 100 parts to about 500 parts, the glycolic component in the range of about 100 parts to about 900 parts, and the reducing agent in the range of about 0.05 part to about 1.0 part, all parts per 100 parts water.

6. An ostomy gasket according to claim 1, wherein the water-soluble reducing agent is selected from the group consisting of hydroquinone, ascorbic acid, araboascorbic acid, erythorbic acid, and mixtures thereof.

7. An ostomy sealing gasket according to claim 1, wherein the absorptive material is a material selected from the group consisting of karaya gum, gum acacia, guar gum, hydroxyethyl cellulose, methyl cellulose, microcrystalline cellulose, fumed silica, and mixtures thereof.

* * * * *